(12) United States Patent
Wilson (10) Patent No.: US 9,877,967 B2
(45) Date of Patent: Jan. 30, 2018

(54) METHODS AND PHARMACEUTICAL COMPOSITIONS FOR PREVENTING AND TREATING RENAL IMPAIRMENT

(75) Inventor: Constance Neely Wilson, Raleigh, NC (US)

(73) Assignee: Endacea, Inc., Research Triangle Park, NC (US)

(*) Notice: Subject to any disclaimer, the term of this patent is extended or adjusted under 35 U.S.C. 154(b) by 1180 days.

(21) Appl. No.: 14/440,395

(22) PCT Filed: Jan. 25, 2011

(86) PCT No.: PCT/US2011/022411
§ 371 (c)(1),
(2), (4) Date: May 4, 2015

(87) PCT Pub. No.: WO2011/094208
PCT Pub. Date: Aug. 4, 2011

(65) Prior Publication Data
US 2015/0283143 A1     Oct. 8, 2015

Related U.S. Application Data

(60) Provisional application No. 61/298,316, filed on Jan. 26, 2010.

(51) Int. Cl.
| | | |
|---|---|---|
| A61K 31/522 | (2006.01) | |
| A61K 45/06 | (2006.01) | |
| A61K 31/519 | (2006.01) | |
| A61K 31/52 | (2006.01) | |

(52) U.S. Cl.
CPC ......... *A61K 31/522* (2013.01); *A61K 31/519* (2013.01); *A61K 31/52* (2013.01); *A61K 45/06* (2013.01)

(58) Field of Classification Search
CPC .............................. A61K 31/522; A61K 45/06
See application file for complete search history.

(56) References Cited

U.S. PATENT DOCUMENTS

| | | | |
|---|---|---|---|
| 5,786,360 A | 7/1998 | Neely | |
| 6,221,338 B1 | 4/2001 | Staniforth | |
| 6,475,523 B1 | 11/2002 | Staniforth | |
| 6,489,332 B1 | 12/2002 | Neely | |
| 6,521,260 B1 | 2/2003 | Staniforth | |
| 6,582,678 B2 | 6/2003 | Staniforth | |
| 6,613,307 B1 | 9/2003 | Cooper | |
| 6,652,837 B1 | 11/2003 | Edwards et al. | |
| 6,680,299 B2 | 1/2004 | Or et al. | |
| 6,680,322 B2 | 1/2004 | Castelhano et al. | |
| 6,680,324 B2 | 1/2004 | Castelhano et al. | |
| 6,941,948 B2 | 9/2005 | Staniforth et al. | |
| 6,948,496 B2 | 9/2005 | Eason et al. | |
| 6,989,155 B1 | 1/2006 | Ganderton et al. | |
| 7,202,252 B2 | 4/2007 | Wilson | |
| 7,247,639 B2 | 7/2007 | Wilson et al. | |
| 2002/0082269 A1 | 6/2002 | Neely | |
| 2003/0170183 A1 | 9/2003 | Staniforth | |
| 2003/0202944 A1 | 10/2003 | Staniforth | |
| 2005/0013862 A1 | 1/2005 | Tobyn et al. | |
| 2005/0152849 A1 | 7/2005 | Staniforth | |
| 2005/0158394 A1 | 7/2005 | Staniforth et al. | |
| 2005/0187226 A1* | 8/2005 | Wilson ............ | C07D 473/06 514/263.2 |
| 2005/0205083 A1 | 9/2005 | Staniforth et al. | |
| 2006/0029552 A1 | 2/2006 | Staniforth | |
| 2007/0161629 A1 | 7/2007 | Wilson et al. | |
| 2007/0274910 A1 | 11/2007 | Wilson et al. | |
| 2008/0027082 A1 | 1/2008 | Hocher et al. | |

FOREIGN PATENT DOCUMENTS

WO     WO 03103675 A2 * 12/2003  ........... A61K 31/522

OTHER PUBLICATIONS

Vallon et al. Handbook of Experimental Pharmacology, 193, (2009), p. 443-470.*
Higuchi et al., "Pro-drugs as Novel Drug Delivery Systems", ACS Symposium Series 14; American Chemical Society: Washington, DC, pp. 1-115, published Jun. 1, 1975.
Roche, Edward (ed.), "Bioreversible Carriers in Drug Design", American Pharmaceutical Association and Pergamon Press, pp. 1-12, 1987.
Dittrich, et al., "The Effect of KW-3902, an Adenosine Al Receptor Antagonist, on Renal Function and Renal Plasma Flow in Ambulatory Patients With Heart Failure and Renal Impairment", Journal of Cardiac Failure, vol. 13, No. 8, pp. 609-617, Oct. 2007.
Dohadwala, et al., "Role of Adenosine Antagonism in the Cardiorenal Syndrome", The Author. Journal Compilation, Blackwell Publishing Ltd., Cardiovascular Therapeutics 26 (2008), pp. 276-286, 2008.
Givertz, et al., "The Effects of KW-3902, an Adenosine A1-Receptor Antagonist, on Diuresis and Renal Function in Patients With Acute Decompensated Heart Failure and Renal Impairment or Diuretic Resistance", ISSN 0735-1097/07, Journal of the American College of Cardiology, vol. 50, No. 16, pp. 1551-1560, Oct. 16, 2007.
Gottlieb, et al., "BG9719 (CVT-124), an A1 Adenosine Receptor Antagonist, Protects Against the Decline in Renal Function Observed With Diuretic Therapy", Circulation 105, pp. 1348-1353, 2002.

(Continued)

*Primary Examiner* — Yong Chu
(74) *Attorney, Agent, or Firm* — James G. Passé; Passé Intellectual Property, LLC (57) ABSTRACT

The present invention relates to methods for treating and preventing renal impairment by administering to a subject a therapeutically effective amount of an $A_1$ adenosine receptor antagonist alone or in combination with at least one additional therapeutic agent. The invention further encompasses pharmaceutical compositions comprising an $A_1$ adenosine receptor antagonist alone or with, at least, one additional therapeutic agent in a pharmaceutically acceptable carrier. The pharmaceutical compositions of the invention find use in methods for treating and preventing renal impairment.

1 Claim, 1 Drawing Sheet

(56) References Cited

OTHER PUBLICATIONS

Osswald, et al., "Methylxanthines and the Kidney", Handbook of Experimental Pharmacology, 200, pp. 391-412, 2011.
International Search Report and the Written Opinion of the International Searching Authority for related case PCT/US2011/022411, dated Oct. 31, 2011.
Vallon et al. "Adenosine receptors and the Kidney" Wilson CN, Mustafa SJ (eds) Adenosine receptors in health and disease, Handbook of Experimental Pharmacology. Springer Verlag Berlin Heidelberg, 193, pp. 443-470, 2009.
Ticho et al., "Renal effects of BG9928, an A1 adenosine receptor antagonist, in rats and nonhuman primates", Drug Dev Res 58:486-492, 2003.
Avis, Kenneth, "Parenteral Preparations" Gennaro AR (Ed) Remington's Pharmaceutical Sciences, 18th edition, Mack Publishing Co., Eaton, Pennsylvania, pp. 1545-1547, 1990.
Gallos et al., "A1 adenosine receptor knockout mice exhibit increased mortality, renal dysfunction, and hepatic injury in murine septic peritonitis", Am J Physiol Renal Physiol 289: F369-F376, 2005, published Mar. 22, 2005.
Givertz, Michael M., "Adenosine A1 Receptor Antagonists at a Fork in the Road," Circ Heart Failure, 2:519-522, American Heart Association, Inc., 2009.
Hess, Sonja, "Recent advances in adenosine receptor antagonist research", Expert Opin. Ther. Patents (2001) 11 (10):1533-1561.
Joo et al., "Acute and delayed renal protection against renal ischemia and reperfusion injury with A1 adenosine receptors", Am J Physiol Renal Physiol 293: F1847-F1857, 2007.
Lee et al., "A1 adenosine receptor knockout mice exhibit increased renal injury following ischemia and reperfusion", Am J Physiol Renal Physiol, 286: F298-F306, 2004.
Lee et al., "Protective effects of renal ischemic preconditioning and adenosine pretreatment: role of A1 and A3 receptors", Am. J. Physiol. Renal Physiol., 278:: F380-F387, 2000.
Lee et al., "A1 Adenosine Receptor Activation Inhibits Inflammation, Necrosis, and Apoptosis after Renal Ischemia—Reperfusion Injury in Mice", J Am Soc Nephrol 15: 102-111, 2004.
Lee et al., "Renal tubule necrosis and apoptosis modulation by A1 adenosine receptor expression", Kidney International (2007), 1249-1261.
Massie et al., "Rolofylline, an Adenosine A1-Receptor Antagonist, in Acute Heart Failure", The New England Journal of Medicine, 363;15, Oct. 7, 2010.
Obiefuna et al., "A Novel A1 Adenosine Receptor Antagonist, L-91-1 [3-[2-(4-Aminophenyl)-ethyl]-8-benzyl-7-{2-hydroxyethyl)-amino]-ethyl}-1-propyl-3, 7-dihydro-purine-2, 6-dioine], Reduces Allergic Responses to House Dust Mite in an Allergic Rabbit Model of Asthma", The Journal of Pharmacology and Experimental Therapeutics, vol. 315, No. 1, JPET 315: 329-336, 2005.

* cited by examiner

METHODS AND PHARMACEUTICAL COMPOSITIONS FOR PREVENTING AND TREATING RENAL IMPAIRMENT

The application claims priority of U.S. provisional application No. 61/298,316 filed on Jan. 26, 2010 and is included herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to methods and compositions for the prevention and treatment of renal impairment. Specifically it relates to prevention and treatment of renal impairment with an $A_1$ adenosine receptor antagonist alone or in combination with at least one additional therapeutic agent.

Description of Related Art

Renal impairment may occur following an acute insult to the kidney, e.g. reduced blood flow to the kidney or the use of contrast dye for radiological procedures or other substances that are toxic to the kidney, i.e. nephrotoxins, and is referred to as acute renal injury or acute renal failure. Depending on the severity of the insult the renal impairment may be reversible and self-limited and is characterized acutely by an increase in serum creatinine and blood urea nitrogen. With acute renal injury urine volume may be reduced. Also, renal impairment is associated with chronic kidney disease. Chronic kidney disease may occur following an acute insult to the kidney, with polycystic kidney disease, nephropathies, such as primary glomerular diseases, diabetes mellitus, autoimmune diseases, long standing hypertension or other forms of cardiovascular disease, e.g. heart failure, is progressive in nature, and is characterized by a reduction in glomerular filitration rate (GFR), creatinine clearance, and urine output, and azotemia or uremia. Chronic renal impairment may be associated with diuretic resistance.

Acute or chronic renal impairment may occur with vascular obstruction of arteries or veins of the kidney, urinary tract outflow obstruction, sepsis, shock, e.g. hypovolemic, hemorrhagic, cardiogenic, or anaphylactic shock, myoglobinuria, hemoglobinuria, hepatic failure, radiation exposure, infections, vasculitis, and following kidney transplant surgery. Also, acute or chronic renal impairment, also referred to as acute or chronic renal insufficiency, may occur with trauma, ischemia, or ischemia and reperfusion of the kidney or other organs, following cardiopulmonary bypass surgery or other surgeries that may result in reduced blood flow to the kidney, with sepsis, or with the use of nephrotoxins, including contrast dyes used in radiological procedures and chemotherapeutic drugs, such as platinum containing chemotherapeutic drugs, e.g. cisplatin. Acute or chronic renal impairment may be associated with asphyxia at birth or with drowning, with mercury poisoning, with the use of glycerol, nonsteroidal anti-inflammatory drugs, e.g. indomethacin, antibiotics, e.g. aminoglycosides, including gentamicin, or with the use of immunosuppressant drugs, e.g. calcineurin inhibitors, including cyclosporine or tacrolimus.

Although adenosine acts as a vasodilator throughout most of the body, in the kidney, by acting on $A_1$ adenosine receptors on preglomerular afferent arterioles, adenosine produces vasoconstriction and a decrease in GFR (Volker and Osswald, Hand Exp Pharmacol, 193:443-470, 2009).

In humans the GFR is high (approximately 180 l/day) and about 99% of the filtered fluid and NaCl are reabsorbed along the tubular and collecting duct system, such that urinary excretion closely matches intake (Volker and Osswald supra). To avoid renal loss or retention of fluid or NaCl, GFR and reabsorption must be closely matched. This is accomplished via tubuloglomerular feedback (TGF). Adenosine is the mediator of TGF. Activation of the TGF mechanism occurs in response to the sensing of the NaCl load in the thick ascending limb (where 85% of the filtered sodium has been reabsorbed) by specialized tubular cells, the macula densa. In response to the NaCl load, these cells release adenosine which, in turn, acts on $A_1$ adenosine receptors on preglomerular afferent arterioles to produce vasoconstriction and reduce GFR, thus producing an inverse relationship between NaCl load and single nephron GFR and limiting the NaCl load to the distal segments. Moreover, activation of $A_1$ adenosine receptors increases sodium reabsorption in proximal tubules and the net effect of $A_1$ adenosine receptor mediated preglomerular afferent arteriolar constriction and decrease in GFR taken together with increased sodium reabsorption produces volume overload.

$A_1$ adenosine antagonists improve renal function in animal models of nephrotoxic acute renal failure (Volker and Osswald supra), in animals with renal impairment due to loop diuretics (Ticho, et al., Drug Dev Res 58:486-492, 2003), such as furosemide, and in humans with chronic heart failure (Dittrich et al., J Cardiac Fail 13:609-617, 2007; Dohadwala et al., Cardiovas Ther 26: 276-286, 2008; Givertz et al., J Am Coll Cardiol 50:1551-1560, 2007, Gottlieb et al., Circulation 105:1348-1353, 2002).

Progressive decline in renal function accompanies heart failure as a function of a progressive decline in cardiovascular function and also, in the case of volume overload, excessive diuresis with the use of standard therapy diuretics, e.g. loop diuretics, including furosemide. However, although most clinicians attribute the decline in renal function to over-diuresis, other contributing factors include activation of the renin-angiotensin aldosterone system (RAAS), adrenergic stimulation, oxidative stress, and inflammation. Also, in patients with persistent volume overload, factors that contribute to a decline in renal function include, renal vasoconstriction, renal venous congestion, drugs that modulate the RAAS, including angiotensin-converting enzyme (ACE) inhibitors, angiotensin receptor blockers, aldosterone antagonists, and high-dose diuretic therapy. Furthermore, although diuretics are the mainstay of treatment for acute volume overload in patients with heart failure, i.e. acute decompensated heart failure (ADHF), resistance to diuretic therapy may develop, requiring escalating the doses of diuretic agents to achieve the desired urine output which, in turn, is associated with a progressive decline in renal function.

A number of pharmaceutical companies have tried to develop $A_1$ adenosine receptor antagonists as commercial products for renal impairment. These attempts have not been successful because of the physiochemical properties of these $A_1$ adenosine receptor antagonists. These compounds have low aqueous solubility. Moreover, low aqueous solubility and special formulations for these $A_1$ adenosine receptor antagonists required for human use may result in low bioavailability to the kidney. Therefore, a need exists for compositions for $A_1$ adenosine receptor antagonists with improved physiochemical characteristics, e.g. high aqueous solubility and higher bioavailability, that are more effective for preventing and treating renal impairment, therefore more suited for commercial use.

BRIEF SUMMARY OF THE INVENTION

The methods of the invention comprise administering to a subject a therapeutically effective amount of an $A_1$ adenosine receptor antagonist. The $A_1$ adenosine receptor antagonist may be administered alone or in combination with at least one additional therapeutic agent to promote a desired prophylactic or therapeutic response. When the $A_1$ adenosine receptor antagonist is administered in combination with at least one therapeutic agent, the $A_1$ adenosine receptor antagonist and the additional therapeutic agent(s) may be administered simultaneously or sequentially.

The methods for preventing and treating renal impairment disclosed herein further comprise administering a pharmaceutical composition to a subject, wherein the pharmaceutical composition comprises an $A_1$ adenosine receptor antagonist, a pharmaceutically acceptable carrier, and optionally at least one additional therapeutic agent.

One particular aspect is a method of preventing or treating renal impairment in a subject, the method comprising administering to the subject a therapeutically effective amount of an $A_1$ adenosine receptor antagonist, wherein the $A_1$ adenosine receptor antagonist comprises a compound of formula (I):

wherein $R_1$ is selected from the group consisting of $C_1$-$C_8$ alkyl;
$R_2$ is of the formula:

wherein n is an integer ranging from 1 to 8; $R_5$ is H or $CH_3(CH_2)_p$, wherein p is an integer ranging from 1 to 7; and $R_6$ is H; $(CH_2)_mH$; or $(CH_2)_mOH$, wherein m is an integer ranging from 1 to 8;
$R_3$ is:

wherein q is an integer ranging from 1 to 8; wherein $R_7$ is selected from the group consisting of H, OH, $NH_2$, $R_9COOH$, wherein $R_9$ is an alkylene or alkenylene group having 1 to 8 carbon atoms, and $(CH_2)_tOH$, wherein t is an integer ranging from 1 to 8; and
$R_4$ is of the formula:

wherein $R_8$ is selected from the group consisting of H, $NH_2$, OH, $(CH_2)_fNH_2$ wherein f is an integer ranging from 1 to 8, $(CH_2)_sOH$, wherein s is an integer ranging from 1 to 8, and $R_{10}COOH$, wherein $R_{10}$ is an alkylene or alkenylene group having 1 to 8 carbon atoms; and r is an integer ranging from 1 to 8, and hydrates, salts, solvates, and prodrugs thereof.

Another aspect is a method of preventing or treating renal impairment in a subject, the method comprising administering to the subject a therapeutically effective amount of a pharmaceutical composition comprising an $A_1$ adenosine receptor antagonist in combination with a pharmaceutically acceptable carrier, wherein the $A_1$ adenosine receptor antagonist comprises the compound of formula (I), wherein:
$R_1$ is $C_3$ alkyl;
$R_2$ is:

wherein n is 2; $R_5$ is $CH_3(CH_2)_p$, wherein p is 1; and $R_6$ is $(CH_2)_mOH$, wherein m is 2;
$R_3$ is:

wherein q is 1; wherein $R_7$ is H; and
$R_4$ is of the formula:

wherein $R_8$ is $NH_2$; and r is 2.

DETAILED DESCRIPTION OF THE INVENTION

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. This detailed description defines the meaning of the terms used herein and specifically describes embodiments in order for those skilled in the art to practice the invention.

Definitions

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language).

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawing(s) featured in the FIGURE(S) are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

The present invention is directed to methods for preventing and treating renal impairment. Herein, "preventing" means administering a therapeutic agent prior to an insult to the kidney to partially or totally prevent it from an impairment in function. "Treating" means administering the agent after an insult, but before manifestation of kidney impairment. The administration can thus mitigate (partially or totally) the onset of impairment. The methods comprise administering to a subject a therapeutically effective amount of an $A_1$ adenosine receptor antagonist alone or in combination with at least one additional therapeutic agent. $A_1$ adenosine receptor antagonists of the present invention are known in the art and include, for example, those compounds described in U.S. Pat. Nos. 5,786,360, 6,489,332, 7,202, 252 B2, 7,247,639 B2, and in co-pending U.S. application Ser. No. 10/560,853, entitled "$A_1$ Adenosine Receptor Antagonists," filed Jun. 7, 2004 and PCT/US2008/087638, entitled "$A_1$ Adenosine Receptor Antagonists," filed Dec. 19, 2008 all of which are herein incorporated by reference.

At least one additional therapeutic agent is selected from the group consisting of steroids, beta-2 agonists, xanthines, adenosine, $A_1$ adenosine receptor agonists, $A_1$ adenosine receptor antagonists, $A_{2a}$ adenosine receptor agonists, $A_{2a}$ adenosine receptor antagonists, $A_{2b}$ adenosine receptor antagonists, $A_{2b}$ adenosine receptor agonists, $A_3$ adenosine receptor agonists, $A_3$ adenosine receptor antagonists, adenosine uptake inhibitors, adenosine kinase inhibitors, $P_{2y}$ purinoceptor agonists, $P_{2x}$ purinoceptor antagonists, tumor necrosis factor (TNF) alpha mAb, TNF alpha antagonists, TNF alpha inhibitors, selectin antagonists, beta-2 integrin blockers, interferon, disease modifying anti-rheumatic drugs (DMARDs), proteasome inhibitors, VAP-1 mAb, rNIF, immunomodulators, NHE inhibitors, monophosphoryl Lipid A (MPL A), mycobacterium, endotoxin, interferon-alpha, granulocyte colony stimulating factor (GCSF), granulocyte-macrophage colony stimulating factor (GMCSF), endotoxin antagonists, anti-sepsis drugs, antifactor IX mAb, p38 MAPK inhibitor, lipid emulsion, ethyl pyruvate, re PAF acetylhydrolase, CD14 receptor antagonist, caspase inhibitors, protease inhibitors, mabs acting on neutrophils or lymphocytes, nitric oxide, nitric oxide scavengers, nitric oxide blockers, nitric oxide synthetase inhibitors, re tissue factor protein inhibitors (re TFPI), bactericidal permeabilizing increasing (BPI) protein fragment, CpG DNA, Mycobacterium vaccae, lactobacillus, modified endotoxin—Lipid A, diuretics, loop diuretics, furosemide, thiazide diuretics, potassium-sparing diuretics, mannitol, osmotic diuretics, vasodilators, nesiritide, nitroprusside, anti-platelet agents, anticoagulants, nitrates, nitroglycerin, calcium channel blockers, beta receptor antagonists, antihypertensives, blood pressure lowering agents, inotropic drugs, dopamine, dobutamine, epinephrine, milrinone, digoxin, digitoxin, digitalis, cardiac glycosides, anti-arrhythmics, anti-histamines, cetirizine, leukotriene receptor antagonists, anticytokines, phosphodiesterase enzyme inhibitors, 5-lipoxygenase inhibitors, platelet activating factor antagonists, thromboxane receptor antagonists, neurokinin receptor antagonists, acridine derivatives, complement inhibitors, complement receptor antagonists, immunosuppressant agents, Cytoxan, cyclophosphamide, glucosamine, cyclosporine, Imuran, penacillamine, azathioprine, methotrexate, gold, antimalarial drugs, mycophenolate mofetil, rituximab, interferons, cytostatics, drugs acting on immunophilins, endothelin receptor antagonists, angiotensin enzyme converting (ACE) inhibitors, angiotensin receptor antagonists, aldosterone inhibitors, aldosterone receptor antagonists, natriuretic peptides, recombinant human B-type natriuretic peptide, vasopressin receptor antagonist, antisense oligonucleotides, anti-IgE, insulin, oral hypoglycemics, smooth muscle relaxants, antibiotics, antiviral agents, antifungal agents, anti-inflammatory agents, nonsteroidal anti-inflammatory drugs (NSAIDs), cyclooxygenase-2 inhibitors, antimetabolites, purine synthesis inhibitors, pyrimidine synthesis inhibitors, macrolides, cancer therapies, radiation therapy, narcotics, surfactants, nutritional supplements, hormonal therapies, oxygen therapy, and combinations thereof.

Combination therapy may include other therapies such as renal dialysis, renal transplantation, ultrafiltration, plasmapheresis, cardiac assist devices, intraaortic balloon counterpulsation, external counterpulsation, or cardiac resynchronization therapy.

Renal impairment may occur following an acute insult to the kidney, e.g. reduced blood flow to the kidney or the use of contrast dye for radiological procedures or other substances that are toxic to the kidney, i.e. nephrotoxins, and is referred to as acute renal injury or acute renal failure. Depending on the severity of the insult the renal impairment may be reversible and self-limited and is characterized acutely by an increase in serum creatinine and blood urea nitrogen. With acute renal injury urine volume may be reduced. Also, renal impairment is associated with chronic kidney disease. Chronic kidney disease may occur following an acute insult to the kidney, with polycystic kidney disease, nephropathies, such as primary glomerular diseases, diabetes mellitus, autoimmune diseases, long standing hypertension or other forms of cardiovascular disease, e.g. heart failure, is progressive in nature, and is characterized by a reduction in glomerular filtration rate (GFR), creatinine clearance, and urine output, and azotemia or uremia. Chronic renal impairment may be associated with diuretic resistance.

Acute or chronic renal impairment may occur with vascular obstruction of arteries or veins of the kidney, urinary tract outflow obstruction, sepsis, shock, e.g. hypovolemic, hemorrhagic, cardiogenic, or anaphylactic shock, myoglobinuria, hemoglobinuria, hepatic failure, radiation exposure, infections, vasculitis, and following kidney transplant surgery. Also, acute or chronic renal impairment, also referred to as acute or chronic renal insufficiency, may occur with trauma, ischemia, or ischemia and reperfusion of the kidney or other organs, following cardiopulmonary bypass surgery or other surgeries that may result in reduced blood flow to the kidney, with sepsis, or with the use of nephrotoxins, including contrast dyes used in radiological procedures and chemotherapeutic drugs, such as platinum containing chemotherapeutic drugs, e.g. cisplatin. Acute or chronic renal impairment may be associated with asphyxia at birth or with drowning, with mercury poisoning, with the use of glycerol, nonsteroidal anti-inflammatory drugs, e.g. indomethacin, antibiotics, e.g. aminoglycosides, including gentamicin, or with the use of immunosuppressant drugs, e.g. calcineurin inhibitors, including cyclosporine or tacrolimus. Methods and laboratory tests for assessing renal impairment (and the improvement or worsening thereof) of are well known in the art.

The term "renal impairment" as used herein is inclusive of renal or kidney failure, renal or kidney insufficiency, renal or kidney malfunction, acute kidney injury, and chronic kidney disease, and related conditions, as well as the clinical symptoms, laboratory and other diagnostic measurements, and complications associated with each of these conditions. The methods of the invention find use, for example, in improvement in renal function, such as increase in GFR, preventing or limiting injury or damage to the kidney, and, and generally improving the outcome of patients with renal impairment.

The methods of the invention comprise administering to a subject a therapeutically effective amount of an $A_1$ adenosine receptor antagonist in combination with at least one additional therapeutic agent. Any method for administering a composition to a subject may be used in the practice of the invention. Examples of possible routes of administration include parenteral, (e.g., intravenous (IV), intramuscular (IM), intradermal, subcutaneous (SC), or infusion), oral, pulmonary (e.g., inhalation), nasal, transdermal (topical), transmucosal, and rectal administration. By "therapeutically effective dose," "therapeutically effective amount," or "effective amount" is intended an amount of the $A_1$ adenosine receptor antagonist that, when administered optionally in combination with at least one other therapeutic agent, brings about a positive therapeutic response with respect to treatment of a subject for renal impairment. In particular embodiments, a therapeutically effective dose of the $A_1$ adenosine receptor antagonist for oral administration is in the range from about 0.1 mg/kg to about 50 mg/kg. In other embodiments, a therapeutically effective dose of the $A_1$ adenosine receptor antagonist for intravenous administration is in the range from about 0.001 mg/kg to about 25 mg/kg.

"Positive therapeutic response" refers to, for example, improvement in at least one of the measurements of renal impairment, preventing the worsening of at least one renal impairment-related measurement, or preventing or limiting the progression of the condition. An improvement in at least one of the measurements of renal impairment can be assessed by a physician using routine laboratory tests (e.g. GFR, creatinine clearance, blood urea nitrogen, or serum creatinine, potassium, or pH), assessment of physiological data, (e.g. urine output), radiological criteria, and other diagnostic criteria or assays used to assess kidney function. Determination of therapeutically effective amounts is well within the capability of those skilled in the art.

The decision to begin the therapy for renal impairment described herein will be based upon the laboratory measurements and other diagnostic criteria that show renal impairment. Typical clinical manifestations are described herein above and include increased serum creatinine, blood urea nitrogen, and a decrease in urine output. With more severe cases a decrease in GFR and creatinine clearance, an increase in serum potassium, and a decrease in blood pH (referred to as acidosis) may be present, in addition, to an increase in serum creatinine, blood urea nitrogen, and decrease in urine output. These and other signs of renal impairment are well known in the art. Alternatively, a physician may choose to initiate the therapeutic methods described herein for a patient at risk of developing renal impairment prior to the appearance of clinical manifestations described herein above.

A physician of ordinary skill in the art can determine when treatment for renal impairment should be initiated and for how long the treatment should continue. Such treatment decisions may be supported by standard clinical laboratory results which monitor the clinical signs of renal impairment. The methods of the invention may be practiced by continuously or intermittently administering a therapeutically effective dose of the $A_1$ adenosine receptor antagonist, optionally in combination with at least one other therapeutic agent, for as long as deemed efficacious for the treatment of renal impairment. The decision to end therapy by the method of the invention may also be supported by standard clinical laboratory results indicating the improvement or disappearance of at least one of the clinical signs of renal impairment. The therapy described herein may be restarted upon the return of renal impairment.

The combination of the $A_1$ adenosine receptor antagonist and at least one other therapeutic agent is administered at a concentration that is therapeutically effective to treat renal impairment. To accomplish this goal, the agents may be formulated using a variety of acceptable excipients known in the art. $A_1$ adenosine receptor antagonists and other therapeutic agents may be administered, for example, by injection, either intravenously, intraperitoneally, intramuscularly, or subcutaneously. Methods to accomplish this administration are known to those of ordinary skill in the art. It may also be possible to obtain compositions which may be topically or orally administered, or which may be capable of transmission across mucous membranes.

The amount of a combination of at least one $A_1$ adenosine receptor antagonist and at least one other therapeutic agent to be administered is readily determined by one of ordinary skill in the art without undue experimentation. Factors influencing the mode of administration and the respective amount of the combination of agents disclosed herein include, but are not limited to, the severity of the disease, the history of the disease, and the age, height, weight, health, medical history (e.g., existence of other diseases such as diabetes, liver disease, and other drugs or treatments the patient is currently taking or has taken in the past), and physical condition of the individual undergoing therapy. Similarly, the amount of the combination of therapeutic agents disclosed herein to be administered will be dependent upon the mode of administration and whether the subject will undergo a single dose or multiple doses of these agents. Generally, a higher dosage is preferred with increasing weight of the patient undergoing therapy.

The treatment of renal impairment described herein can be accomplished with varying doses as well as dosage regimens. Treatment regimens will be based on doses and dosing schedules that maximize therapeutic effects. The therapeutically effective amount of a combination of an $A_1$ adenosine receptor antagonist and the at least one other therapeutic agent can be readily determined by one of ordinary skill in the art without undue experimentation. In particular embodiments, the therapeutically effective dose of a combination of an $A_1$ adenosine receptor antagonist and at least one other therapeutic agent may comprise doses of the individual agents that, when administered alone, would not be therapeutically effective or would be less therapeutically effective than when administered in combination with each other. Thus, when an $A_1$ adenosine receptor antagonist of the invention and another therapeutic agent are administered in combination, a synergistic therapeutic effect may be observed. "Synergistic therapeutic effect" refers to a therapeutic effect observed with a combination of two or more therapies (in this case, the $A_1$ adenosine receptor antagonist and a diuretic, an inotrope, an anti-inflammatory agent, antihypertensive agent, or an immunosuppressant agent) wherein the therapeutic effect (as measured by any of a number of parameters) is greater than the sum of the respective individual therapeutic effects observed with the respective individual therapies. The combination of an $A_1$ adenosine receptor antagonist and an at least one other therapeutic agent may produce a synergistic effect that permits a reduction in the dosages of these agents and an improvement of the clinical outcome of the subject being treated. A reduced dose of the $A_1$ adenosine receptor antagonist and the at least one other therapeutic agent may in turn reduce unwanted side effects associated with each agent.

In some embodiments of the invention, the method comprises administration of multiple doses of an $A_1$ adenosine receptor antagonist in combination with multiple doses of the at least one other therapeutic agent. The method may comprise administration of 1, 2, 3, 4, 5, 6, 7, 8, 9, 10, 15, 20, 25, 30, 35, 40, or more therapeutically effective doses of a pharmaceutical composition comprising either an $A_1$ adenosine receptor antagonist, the at least one other therapeutic agent, or both. The frequency and duration of administration of multiple doses of the pharmaceutical compositions can be readily determined by one of skill in the art without undue experimentation. Moreover, treatment of a subject with a therapeutically effective amount of a combination of an $A_1$ adenosine receptor antagonist and an at least one other therapeutic agent can include a single treatment or can include a series of treatments. It will also be appreciated that the effective dosage of an $A_1$ adenosine receptor antagonist or an at least one other therapeutic agent used for treatment may increase or decrease over the course of a particular treatment. Changes in dosage may result and become apparent from the results of laboratory measurements and other diagnostic measurements or assays known in the art.

In some embodiments, the $A_1$ adenosine receptor antagonist comprises a compound of formula (I):

(I)

wherein $R_1$ is selected from the group consisting of $C_1$-$C_8$ alkyl;

$R_2$ is of the formula:

wherein n is an integer ranging from 1 to 8; $R_5$ is H or $CH_3(CH_2)_p$, wherein p is an integer ranging from 1 to 7; and $R_6$ is H; $(CH_2)_mH$; or $(CH_2)_mOH$, wherein m is an integer ranging from 1 to 8;

$R_3$ is:

wherein q is an integer ranging from 1 to 8; wherein $R_7$ is selected from the group consisting of H, OH, $NH_2$, $R_9COOH$, wherein $R_9$ is an alkylene or alkenylene group having 1 to 8 carbon atoms, and $(CH_2)_tOH$, wherein t is an integer ranging from 1 to 8; —and $R_4$ is of the formula:

wherein $R_8$ is selected from the group consisting of H, $NH_2$, OH, $(CH_2)_fNH_2$ wherein f is an integer ranging from 1 to 8, $(CH_2)_sOH$, wherein s is an integer ranging from 1 to 8, and $R_{10}COOH$, wherein $R_{10}$ is an alkylene or alkenylene group having 1 to 8 carbon atoms; and r is an integer ranging from 1 to 8, and, pharmaceutically acceptable salts, hydrates, solvates, and prodrugs thereof.

Methods for synthesizing the $A_1$ adenosine receptor antagonists of the invention are known in the art and are described in, for example, U.S. Pat. Nos. 5,786,360, 6,489,332, 7,202, 252 B2, and 7,247,639 B2.

In a particular aspect of the invention, the $A_1$ adenosine receptor antagonist is 3-[2-(4-aminophenyl)-ethyl]-8-benzyl-7-{2-[ethyl-(2-hydroxyethyl)-amino]-ethyl}-1-propyl-3,7-dihydropurine-2,6-dione, designated L-97-1, and comprises the compound of formula (I), wherein:

$R_1$ is $C_3$ alkyl;

$R_2$ is:

wherein n is 2; $R_5$ is $CH_3(CH_2)_p$, wherein p is 1; and $R_6$ is $(CH_2)_mOH$, wherein m is 2;

$R_3$ is:

wherein q is 1; wherein $R_7$ is H; —and
$R_4$ is of the formula:

wherein $R_8$ is $NH_2$; and r is 2.

The methods of treatment of the present invention are not intended to be limited to particular subjects. A variety of subjects, particularly mammals, is contemplated. Subjects of interest include but are not limited to humans, dogs, cats, horses, pigs, cows, and rodents. In particular embodiments, the subject is a human. The subjects of the invention may be suffering from renal impairment or may be at risk of renal impairment.

Many of the $A_1$ adenosine receptor antagonist compounds of the present invention can be provided as solvates, hydrates, and salts with pharmaceutically compatible counterions. Such pharmaceutically acceptable base addition salts are those salts that retain the biological effectiveness and properties of the free acids, and that are obtained by reaction with suitable inorganic or organic bases. The $A_1$ adenosine receptor antagonists of the invention may form pharmaceutically acceptable salts with both organic and inorganic acids and bases. Exemplary weak organic acids for salt formation include, but are not limited to, acetic acid, beta-alanine, dl-alanine, D-alanine, L-alanine, formic acid, propanoic acid, butyric acid, palmetic acid, oleic acid, sebacic acid, cinnamic acid, adipic acid, citric acid, ascorbic acid (vitamin C), lactic acid, malic acid, maleic acid, fumaric acid, tartartic acid, dl-glutamic acid, D-glutamic acid, L-glutamic acid, dl-aspartic acid, D-aspartic acid, L-aspartic acid, glycine, succinic acid, glutaric acid, gluconic acid, benzoic acid, p-chlorobenzoic acid, p-hydroxybenzoic acid, p-methoxybenzoic acid, o-hydroxybenzoic acid (salicylic acid), 1-hydroxy-2-naphthoic acid, 3-hydroxy-2-naphthoic acid, and the like. Strong organic acids that may be used for salt formation include, for example, benzenesulfonic acid, p-toluenesulfonic acid, m-nitrobenzenesulfonic acid, methanesulfonic acid, ethanesulfonic acid, 1-naphthalenesulfonic acid, 2-naphthalenesulfonic acid, laurylsulfonic acid, and the like. Examples of strong inorganic acids for salt formation include hydrochloric acid, hydrobromic acid, hydroiodic acid, sulfuric acid, phosphoric acid, nitric acid, sodium bisulfate, potassium bisulfate, sodium hydrogen phosphate, potassium hydrogen phosphate, boric acid, xinafoic acid (i.e., xinafoate salt is formed with 1-hydroxy-2-naphthoic acid) and the like.

A xinafoate salt (1-hydoxy-2-napthoic acid) of an $A_1$ adenosine receptor antagonist may be administered to prevent or treat renal impairment. Because xinafoate salts are known to be largely insoluble and to exhibit reduced oral absorption, such salts may be particularly potent, safe, and efficacious when administered by pulmonary inhalation. Inhalational therapy with a xinafoate salt of an $A_1$ adenosine receptor antagonist of the invention may minimize negative systemic effects associated with the traditional $A_1$ adenosine receptor antagonist agents.

Many of the $A_1$ adenosine receptor antagonist compounds of the present invention can be provided as pro-drugs thereof, in accordance with known techniques, to carry out the methods described herein. The term "prodrug" refers to compounds that are transformed in vivo to yield the parent compound of the above formulae, for example, by hydrolysis in blood. A thorough discussion is provided in T. Higuchi and V. Stella, Prodrugs as Novel Delivery Systems, Vol. 14 of the A.C.S. Symposium Series and in Edward B. Roche, ed., Bioreversible Carriers in Drug Design, American Pharmaceutical Association and Pergamon Press, 1987. See also U.S. Pat. No. 6,680,299. Examples include, but are not limited to, a prodrug that is metabolized in vivo by a subject to an active drug having at least some of the activity of the active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

The $A_1$ adenosine receptor antagonist, whether provided alone or in combination with at least one other therapeutic agent such as a diuretic, is typically provided by standard techniques within a pharmaceutically acceptable buffer; for example, sterile saline, sterile buffered water, propylene glycol, combinations of the foregoing, etc. The $A_1$ adenosine receptor antagonist and additional therapeutic agents can be formulated in separate pharmaceutical compositions, or can be formulated within a single pharmaceutical composition for simultaneous administration. Methods for preparing parenterally administrable agents are described in *Remington's Pharmaceutical Sciences* (18$^{th}$ ed.; Mack Publishing Company, Eaton, Pa., 1990), herein incorporated by reference.

The $A_1$ adenosine receptor antagonists of the invention can be administered alone, but may also be administered in admixture with a pharmaceutically acceptable carrier selected with regard to the intended route of administration and pharmaceutical practice. Thus, a pharmaceutical composition of the invention is formulated to be compatible with its intended route of administration. Examples of possible routes of administration include parenteral, [e.g., intravenous (IV), intramuscular (IM), intradermal, subcutaneous (SC), intraperitoneal (IP), intrathecal, or infusion], oral, pulmonary (e.g., inhalation), nasal, transdermal (topical), transmucosal, and rectal administration.

A "pharmaceutically acceptable carrier" refers to a carrier that is conventionally used in the art to facilitate the storage, administration, or the therapeutic effect of the active ingredient. A suitable carrier may also reduce any undesirable side effects of the $A_1$ adenosine receptor antagonist or the at least one additional therapeutic agent in the case of combination therapy. It should not produce significant local or systemic adverse effects in recipients at the dosages and concentrations employed for treatment. Pharmaceutically acceptable carriers of the invention may further comprise surfactants, such as those disclosed in U.S. Pat. Nos. 6,652,837 and 6,613,307, which are herein incorporated by reference in their entirety.

Methods for formulating pharmaceutical compositions are generally known in the art. A thorough discussion of formulation and selection of pharmaceutical acceptable carriers, stabilizers, and isomolytes can be found in *Remington's Pharmaceutical Sciences* (18$^{th}$ ed.; Mack Publishing Company, Eaton, Pa., 1990), herein incorporated by reference.

When a composition of the invention is administered by intravenous, intrathecal, intradermal, or subcutaneous injection, the composition is in the form of a pyrogen-free, parenterally acceptable aqueous solution. The preparation of such parenterally acceptable solutions, having due regard to pH, isotonicity, stability, and the like, is well within the skill in the art. Solutions or suspensions used for parenteral, intrathecal, intradermal, subcutaneous, or intravenous application can include the following components: a sterile diluent such as water for injection, saline solution, fixed oils, polyethylene glycols, glycerin, propylene glycol or other synthetic solvents; such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, multiple dose vials made of glass or plastic, or plastic bags of intravenous solutions, e.g. dextrose, ringers lactate or normal saline.

The $A_1$ adenosine receptor antagonists of the invention can be formulated for parenteral administration by injection, e.g., by bolus injection or continuous infusion. Formulations for injection can be presented in unit dosage form, e.g., in ampoules or in multidose containers, with an added preservative. The compositions can take such forms as suspensions, solutions, or emulsions in oily or aqueous vehicles, and can contain formulatory agents such as suspending, stabilizing, and/or dispersing agents.

For oral administration, the $A_1$ adenosine receptor antagonists can be formulated by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, $A_1$ adenosine receptor antagonists of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch. Methods and devices for administering compositions via pulmonary inhalation and for producing particles suitable for such administration are disclosed in the art. See, for example, U.S. Pat. Nos. 6,221,338, 6,475,523, 6,521,260, 6,582,678, 6,941,948, 6,948,496, 6,989,155; U.S. Patent Application Publication Nos. 2003/0170183, 2003/0202944, 2005/0013862, 2005/0152849, 2005/0158394, 2005/0205083, and 2006/0029552; all of which are herein incorporated by reference in their entirety.

The exact formulation, route of administration, and dosage of the $A_1$ adenosine receptor antagonist and the at least one other therapeutic agent can be chosen by the individual physician in view of the patient's condition. Dosage amount and dosing intervals can be adjusted individually to provide plasma levels of the $A_1$ adenosine receptor antagonist and the at least one other therapeutic agent that are sufficient to maintain positive therapeutic effects.

One of skill in the art will appreciate that the methods for treating renal impairment disclosed herein can be combined with any other therapy for renal impairment. Such therapies include but are not limited to fluid therapy, vasopressor therapy, inotropic therapy, steroid administration, blood product administration, mechanical ventilation, glucose control, insulin therapy, antibiotics, anti-inflammatory agents, immunosuppressant agents, anti-hypertensive agents, diuretics, and oxygen therapy. Combination therapy may include other therapies such as renal dialysis, renal transplantation, ultrafiltration, plasmapheresis, cardiac assist devices, intraaortic balloon counterpulsation, external counterpulsation, or cardiac resynchronization therapy.

The present invention also provides for the use of an $A_1$ adenosine receptor antagonist in the manufacture of a medicament for treating a subject for renal impairment, wherein the medicament is coordinated with treatment using an at least one other therapeutic agent. By "coordinated" is intended that the medicament comprising the $A_1$ adenosine receptor antagonist is to be used either prior to, during, or after treatment of the subject using the at least one other therapeutic agent. "Treatment" in the context of coordinated use of a medicament comprising an $A_1$ adenosine receptor antagonist described herein with one or more other therapeutic agents is herein defined as the application or administration of the medicament or of the other therapeutic agent to a subject, where the subject has renal impairment, a laboratory or diagnostic measurement or assay associated with renal impairment, or a predisposition toward development of renal impairment, where the purpose is to cure, heal, alleviate, relieve, alter, remedy, ameliorate, improve, or affect the renal condition, any associated measurement of renal impairment, or the predisposition toward the development of renal impairment.

EXPERIMENTAL

Example 1: Evaluation of L-97-1 in Treatment of Rats Exposed to High Dose Furosemide and a Low Sodium Diet and Renal Impairment A. Experimental Design and Treatment Groups Groups of 8 male Sprague-Dawley rats weighing 250±20 g are employed. Rats are given an oral dose of furosemide at 100 mg/kg on day −7 and then placed on a low sodium diet (0.03% $Na^+$ wt/wt) for 7 days prior to use in acute experiment (day 0). Furosemide alone, L-97-1 alone, or furosemide in combination with L-97-1 are administered. L-97-1 is administered by oral gavage. Furosemide is administered IV. A 5-hr urine collection is performed. Terminal bleed is collected for measurements of serum electrolytes ($Na^+$ and $K^+$) and creatinine. Urine volume is measured and then centrifuged (400 g, 10 min) and assayed for $Na^+$ and $K^+$ concentrations, and creatinine with an Automatic Analyzer (Toshiba, TBA 1200 FR). Urine volume and urinary electrolytes are calculated and expressed per 100 g of animal body weight. The study design is presented in the table below:

Protective Effect of L-97-1 against Renal
Impairment in Low-Sodium Rats: Study Design

| Group | Test Article | Route | Conc. mg/ml | Dosage ml/kg | Dosage mg/kg | Rats[c] (Male) |
|---|---|---|---|---|---|---|
| 1 | Furosemide + Vehicle[a] | IV | 6 NA | 5 + 10 | 30 + NA | 8 |
| 2 | Furosemide + L-97-1 | IV + PO | 6 5 | 5 + 10 | 30 + 50 | 8 |
| 3 | Vehicle[b] + L-97-1 | PO | NA + 5 | 5 + 10 | NA + 50 | 8 |
| 4 | Vehicle + Vehicle | IV + PO | NA + NA | 5 + 10 | NA + NA | 8 |

[a]Sterile water as vehicle
[b]Sterile 0.9% saline as vehicle
[c]A 5-hr urine collection was performed to measure endogenous creatinine clearance.

Measurements of Electrolytes, Creatinine, Creatinine Clearance, and Fractional Excretion of Sodium The total electrolytes (sodium and potassium) and creatinine in serum and urine are measured. Urine volume was collected over 5 hr. The 24-hr values for creatinine clearance and the fractional excretion of sodium are extrapolated from the 5-hr values. The 5-hr endogenous creatinine clearance ($C_{Cr}$) is used as a measure of glomerular filtration rate. The formulas are as follows:

$$C_{Cr}(\text{ml}/5\text{ hr}) = [U_{Cr} (\text{mg/dL}) \times V (\text{ml}/5\text{ hr})]/S_{Cr} (\text{mg/dL})$$

The 5-hr urinary excretion of sodium ($Na^+$) or potassium ($K^+$) is computed as follows:

$$U_{Na}V (\mu Eq/5 \text{ hr}) = U_{Na} (\mu Eq/ml) \times V (\text{ml}/5 \text{ hr})$$

$$U_{K}V (\mu Eq/5 \text{ hr}) = U_{K} (\mu Eq/ml) \times V (\text{ml}/5 \text{ hr})$$

The fractional excretion of $Na^+$ ($FE_{Na}$), or percentage of the filtered sodium that is excreted into the final urine, is a measure of tubular $Na^+$ reabsorptive function. It is computed as follows:

$$FE_{Na} = 100 \times [U_{Na} (\mu Eq/ml) \times V (\text{ml}/5 \text{ hr})]/S_{Na} (\mu Eq/ml) \times Ccr (\text{ml}/5 \text{ hr})$$

Data Analysis

The mean±SEM values for each treatment group is calculated. Dunnett's test is applied for comparison between vehicle and treated groups. Student's t test for unpaired data is applied for comparison between groups. Difference are considered significant at $P<0.05$.

Figure 1:
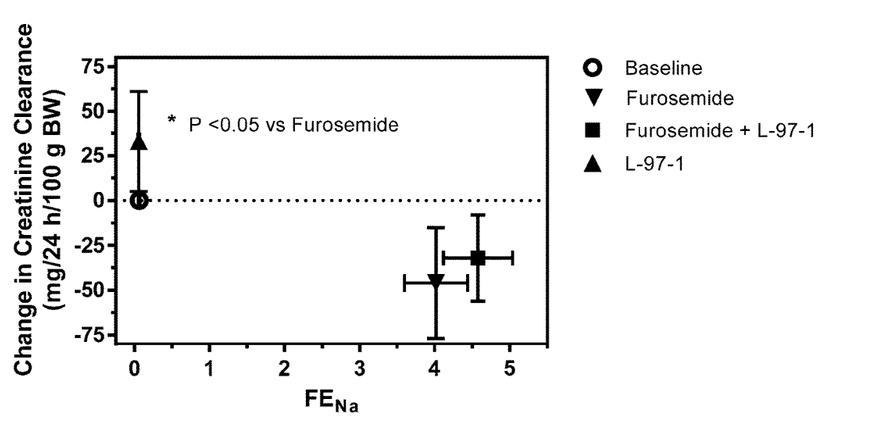
FIG. 1 provides the effect of L-97-1 alone versus furosemide alone or furosemide plus L-97-1 on the change in creatinine clearance (Ccr) [ml/24 h/100 gm Body weight (B.W.)] as a function of fractional excretion of sodium ($FE_{Na}$) in rats exposed to high dose furosemide and a low sodium diet and renal impairment. The values are extrapolated from the 5-hr values. Experimental details are provided in Example 1.

B. Results:

Change in creatinine clearance (Ccr) [ml/24 h/100 gm Body Weight (B.W.)] results are provided in FIG. 1. Change in Ccr, a measure of glomerular filtration rate and renal function, represents the change in Ccr from baseline Ccr, i.e. the Ccr for control rats in Group 4 treated with vehicle alone. Change in Ccr in rats treated with L-97-1 alone (Group 3) is significantly increased compared to the change in Ccr for rats treated with furosemide alone (Group 1) ($P<0.05$). Also, change in Ccr for rats treated with furosemide plus L-97-1 (Group 2) is increased compared to the change Ccr for rats treated with furosemide alone (Group 1).

BIBLIOGRAPHY

1. Vallon V, Osswald H (2009). *Adenosine receptors and the kidney*. In Wilson C N, Mustafa S J (eds) *Adenosine receptors in health and disease, Handbook of Experimental Pharmacology*. Springer-Verlag Berlin Heidelberg, 193, pp 443-470.
2. Dittrich H C, Gupta D, Hack T C, Dowling T, Callahan J, Thomson S (2007). *The effect of KW-3902, an adenosine A1 receptor antagonist, on renal function and renal plasma flow in ambulatory patients with heart failure and renal impairment*. J Cardiac Fail 13:609-617.
3. Dohadwala M M, Givertz M M (2008). *Role of adenosine antagonism in cardiorenal syndrome*. Cardiovascular Therapeutics 26: 276-286.
4. Givertz M M, Massie B M, Fields T K, Pearson L L, Dittrich H C, on behalf of the CKI-201 and CKI-202 investigators (2007). *The effects of KW-3902, an adenosine $A_1$-receptor antagonist, on diuresis and renal function in patients with acute decompensated heart failure and renal impairment or diuretic resistance*. J Am Coll Cardiol 50:1551-1560.
5. Gottlieb S S, Brater C, Thomas I, Havranek E, Bourge R, Goldman S, Dyer F, Gomez M, Bennett D, Ticho B, Beckman E, Abraham W T (2002). *BG9719 (CVT-124), an A1 adenosine receptor antagonist, protects against the decline in renal function observed with diuretic therapy*. Circulation 105:1348-1353.
6. Ticho B, Whalley E, Gill A, Lutterodt F, Jin X, Auchampach J, Smits G (2003). *Renal effects of BG9928, an A1 adenosine receptor antagonist, in rats and nonhuman primates*. Drug Dev Res 58:486-492.
7. Osswald H, Schnermann J (2011). *Methylxanthines and the kidney*. In Fredholm B B (ed) *Methylxanthines, Handbook of Experimental Pharmacology*. Springer-Verlag Berlin Heidelberg, 200, pp 391-412.

What is claimed is:

1. A method of increasing creatinine clearance at a low fractional excretion of sodium in a subject, the method consisting of administering to the subject a therapeutically effective amount of a pharmaceutical composition consisting of an $A_1$ adenosine receptor antagonist alone as a therapeutic agent, in combination with a pharmaceutically acceptable carrier, wherein the $A_1$ adenosine receptor antagonist is 3-[2-(4-aminophenyl)-ethyl]-8-benzyl-7-{2-[ethyl-(2-hydroxyethyl)-amino]-ethyl}-1-propyl-3,7-dihydropurine-2,6-dione.

* * * * *